US006500936B2

United States Patent
Vertesy et al.

(12)

(10) Patent No.: US 6,500,936 B2
(45) Date of Patent: Dec. 31, 2002

(54) PLURAFLAVINS AND DERIVATIVES THEREOF, PROCESS FOR THEIR PREPARATION AND USE THEREOF

(75) Inventors: Laszlo Vertesy, Eppstein-Vockenhausen (DE); Klaus Ehrlich, Rüsselsheim (DE); Martin Knauf, Root (CH); Joachim Wink, Rödermark (DE); Francis P. Barbone, Annandale, NJ (US); Elaine A. Powers, High Bridge, NJ (US); Elizabeth A. Cashman, Bridgewater, NJ (US)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 69 days.

(21) Appl. No.: 09/784,035

(22) Filed: Feb. 16, 2001

(65) Prior Publication Data

US 2002/0028921 A1 Mar. 7, 2002

(30) Foreign Application Priority Data

Feb. 18, 2000 (EP) .............................. 00103540

(51) Int. Cl.[7] ........................ A61K 31/35; A61K 31/70; C07H 15/24
(52) U.S. Cl. ....................... 536/6.4; 536/4.1; 536/17.2; 536/14; 536/16.8; 536/18.5; 514/27; 514/34; 514/62; 514/453; 549/384; 435/125
(58) Field of Search ................ 536/6.4, 17.2, 536/14, 16.8, 18.5, 4.1; 514/27, 34, 62, 453; 549/384; 435/125

(56) References Cited

U.S. PATENT DOCUMENTS

| 4,847,387 A | * | 7/1989 | Nakano et al. | ............. 549/384 |
| 5,001,058 A | * | 3/1991 | Konishi et al. | ............. 435/125 |
| 5,168,100 A | * | 12/1992 | Abe et al. | ................... 514/453 |

FOREIGN PATENT DOCUMENTS

WO    WO 90/09435    8/1990

OTHER PUBLICATIONS

Vertesy et al. "Pluraflavins, potent antitumor antibiotics from Saccharothiy sp. DSM 12931." J. of Antibiotics, vol. 54, No. 9, pp. 718–729, 2001.*
Brill, G.M., "Altromycins E, F, G, H and I; Additional Novel Components of the Altromycin Complex," *The Journal of Antibiotics*, 47:1160–1164 (1994).
The Merck Index, 12, Ed., p. 463.
The Merck Index, 12, Ed., p. 1025.
The Merck Index, 12, Ed., p. 1704.
The Merck Index, 12, Ed., p. 479.
The Merck Index, 12, Ed., p. 581–582.
Kondo, S., et al., "Structures of Pluramycin A and Neopluramycin, *The Journal of Antibiotics*," 30:1143–1145 (1977).
Abe, N., "Novel Antitumor Antibiotics, Saptomycins II. Isolation, Physico–Chemical Properties and Structure Elucidation," *The Journal of Antibiotics*, 46:1536–1549 (1993).
Sato, Y., et al., "Ankinomycin, A Project Antitumor Antibiotic," *The Journal of Antibiotics*, 42:149–152 (1989).
Kanda, N., "A New Antitumor Antibiotic Kidamycin. I Isolation, Purification and Properties of Kidamycin," *The Journal of Antibiotics*, 24:599–606 (1971).
Sequin, U., "The Structure of the Antibiotic Hedamycin–II," *Tetrahedron*, 34:761–767 (1978).
Brill, G.M., et al., "Altromycins, Novel Pluramycin–Like Antibiotics," The Journal of Antibiotics, 43:229–237 (1990).

* cited by examiner

*Primary Examiner*—Samuel Barts
*Assistant Examiner*—Devesh Khare
(74) *Attorney, Agent, or Firm*—Finnegan, Henderson, Farabow, Garrett & Dunner, L.L.P.

(57) ABSTRACT

The invention relates to a compound of formula (I)

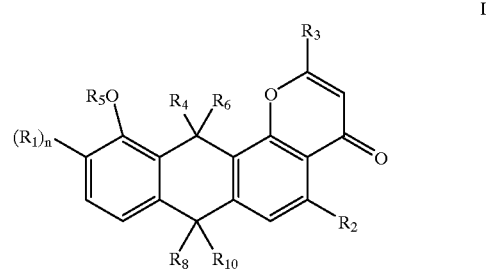

wherein $R_1$ is a sugar; $R_2$ is —$CH_2$—O—($R_7$)m, $R_7$ representing a sugar, or is —COOH; $R_3$ is an epoxide-comprising group, or is $C_1$–$C_6$-alkyl or $C_2$–$C_6$-alkenyl, unsubstituted or substituted by at least one OH; $R_5$ is H, $C_1$–$C_6$-alkyl, $C_2$–$C_6$-alkenyl or $C_2$–$C_6$-alkynyl; $R_4 R_6$, $R_8$ and $R_{10}$ independently of one another are H; $C_1$–$C_6$-alkyl, $C_2$–$C_6$-alkenyl, $C_2$–$C_6$-alkynyl, —$X_2$H, or —$X_2 R_{12}$, or $R_4$ and $R_6$ together and/or $R_8$ and $R_{10}$ together are =$X_2$; $X_2$ is O, NH, N—$C_1$–$C_6$-alkyl, N—$C_2$–$C_6$-alkenyl, N-$C_2$–$C_6$-alkynyl or S; $R_{12}$ is $C_1$–$C_6$-alkyl, $C_2$–$C_6$—alkenyl, $C_2$–$C_6$-alkynyl, aryl or acyl; and m and n are 1 or 2; in any of its stereochemical forms and mixtures of these forms in any ratio, and a physiologically acceptable salt or derivative thereof. The compounds are obtainable from a culture of the microorganism Actinomycetales species HAG 003959, DSM 12931, by fermentation. Accordingly, the invention relates to a process for their preparation and to the use of the compounds as pharmaceuticals, for example as antitumor agents.

27 Claims, No Drawings

PLURAFLAVINS AND DERIVATIVES THEREOF, PROCESS FOR THEIR PREPARATION AND USE THEREOF

The present invention relates to novel compounds of formula I

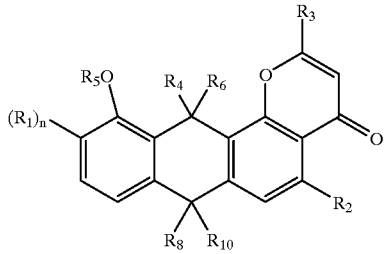

wherein $R_1$, $R_2$, $R_3$, $R_4$, $R_5$, $R_6$, $R_8$, $R_{10}$ and n are as defined below. The compounds of formula I inhibit transcriptase, have a cytostatic action and are particularly suitable for treating tumors. The compounds of formula I can be obtained by growing Actinomycetales species HAG 003959, DSM 12931, in a culture medium. Accordingly, the invention relates to a process for preparing the compounds of formula I the use of the compounds for preparing a pharmaceutical for the treatment of malignant disorders and of diseases which can be treated by inhibiting transcriptase, and to pharmaceutical preparations comprising at least one compound of formula I.

Cancer is a disease of humans and animals which is in most cases fatal and which is generally caused by the uncontrolled growth of endogenous cells. Cancer is the term used for the formation of malignant tumors (malignancy), of neoplasms (tumors or carcinomas) or for the malignant degeneration and dysmaturity of white blood cells (leukemia). Cancer or tumor cells are generally formed by transformation of endogenous cells. The malignancy of the cancer cell expresses itself in the autonomy of growth, i.e. its capability of growing uninhibitedly and without integration into the organ system and infiltrating, with destruction of tissue. A sure sign of malignancy is the formation of metastases far from the tumor after hematogenic or lymphogenic spreading of tumor cells. Cancer is one of the most frequent causes of death in humans, and there is therefore a great demand for methods and agents for curing or treating malignant degenerations.

In addition to the radical approach of surgical removal of the tumor, the options for therapy of malignant tumors include radiotherapy with X-rays, α-, β-, γ-rays, immunotherapy and chemotherapy. As yet, the use of immunotherapy is limited. Chemotherapy of tumors is understood as meaning administration of cell toxins (cytostatics) for the treatment of tumors and remaining tumor cells generally after local surgical treatment or irradiation. These substances intervene specifically in certain processes of cell division, so that tissues having a high proportion of dividing cells, such as the rapidly growing tumor tissue, react sensitively. The agents used are alkylating compounds, such as, for example, cyclophosphamide (The Merck Index, 12th Ed. page 463), antimetabolites, such as methotrexate (The Merck Index, 12th Ed. page 1025), alkaloids, such as vincristine (The Merck Index, 12th Ed. page 1704) and antibiotics, such as daunomycin (The Merck Index, 12th Ed. page 479), and adriamycin (The Merck Index, 12th Ed. pages 581–582). However, owing to massive side-effects, all these agents have significant disadvantages, so that the death of the diseased person can, in many cases, only be delayed, but not prevented. Furthermore, degenerated (cancer) cells become resistant to the agents used; in this case, the conventional pharmaceuticals no longer have any cytostatic action, but they are toxic, owing to the side-effects. Furthermore, it has been found that a combined and/or sequential use of cytostatics exceeds the activity of an individual cytostatic (monotherapy), and it is therefore possible that the considerable side-effects in polychemotherapy are non-additive. For all these reasons, novel chemotherapeutics are urgently required and thus investigated world-wide.

Surprisingly, it has been found that the microorganism strain Actinomycetales species HAG 003959, DSM 12931, is capable of producing highly effective novel cytostatics which inhibit cell growth even at very low concentrations. Hereinbelow, the novel compounds are referred to as pluraflavins, and they form, together with pluraflavin derivatives, part of the subject matter of the invention. The pluraflavins are antibiotics which comprise a p-quinoid ring skeleton and various sugar building blocks. They inhibit transcription by intercalation of nucleic acid double strands and, if appropriate, additional alkylation. The ring skeleton was described for the first time by S. Kondo et al. in Journal of Antibiotics, volume 30, pages 1143–1145, 1977, as a part of pluramycin. Later, this ring skeleton was found in a plurality of antibiotics; in addition to pluramycin and neopluramycin, the compounds saptomycines (N. Abe et al. J. Antibiotics, 46, 1536–1549, 1993), ankinomycin (Y. Sato et al. J. Antibiotics 42, 149, 1989), kidamycin (N. Kanda et al. J. Antibiotics, 24, 599, 1971), hedamycin (U. Sequin et al. Tetrahedron, 34, 761, 1978) and the altromycines (G. M. Brill et al. J. Antibiotics, 43, 229–237, 1990) have been described as structurally related compounds. The prior art substances often have disadvantages which manifest themselves in an unsatisfactory efficacy, high toxicity and/or undesirable side-effects.

Accordingly, the present invention relates to compounds of formula (l)

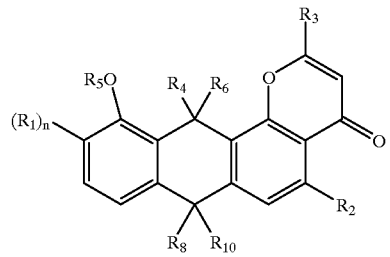

wherein
$R_1$ is a sugar,
$R_2$ is —COOH or —CH$_2$—O—(R$_7$)m, wherein $R_7$ is a sugar group,
$R_3$ is chosen from epoxide-comprising groups, $C_1$–$C_6$-alkyl groups, and $C_2$–$C_6$-alkenyl groups, wherein said alkyl and alkenyl groups are optionally substituted with at least one OH group,
$R_5$ is chosen from H, $C_1$–$C_6$-alkyl, $C_2$–$C_6$-alkenyl and $C_2$–$C_6$-alkynyl,
$R_4$, $R_6$, $R_8$ and $R_{10}$, are each independently chosen from H, $C_1$–$C_6$-alkyl, $C_2$–$C_6$—alkenyl, $C_2$–$C_6$—alkynyl, —X$_2$H, and -X$_2$R$_{12}$, or
$R_4$ and $R_6$ together and/or $R_8$ and $R_{10}$ together are =X$_2$,
$X_2$ is O, NH, N-$C_1$–$C_6$—alkyl, N-$C_2$–$C_6$—alkenyl, N-$C_2$–$C_6$-alkynyl or S,
$R_{12}$ is $C_1$–$C_6$—alkyl, $C_2$–$C_6$-alkenyl, $C_2$–$C_6$-alkynyl, aryl or acyl, and
m and n, independently of one another, are 1 or 2,
in all their stereochemical forms and mixtures of these forms in any ratio, and their physiologically acceptable salts and derivatives.
In formula (I)
$C_1$–$C_6$-alkyl is a straight-chain or branched alkyl having from 1 to 6 carbon atoms, for example, methyl, ethyl, isopropyl, tert-butyl and hexyl, $C_2$–$C_6$-alkenyl is a straight-chain or branched alkenyl having from 2 to 6 carbon atoms, for example, allyl, crotyl and pentenyl, and $C_2$–$C_6$-alkynyl is a straight-chain or branched alkynyl having from 2 to 6 carbon atoms, for example, propynyl, butynyl and pentynyl.

Aryl is an aromatic ring structure, for example, phenyl, benzyl or 1- or 2-naphthyl. Aryl may be optionally substituted, for example by halogen, such as chlorine, bromine, fluorine, by alkyl having 1–4 carbon atoms, for example, methyl, by hydroxyl, by alkoxy having 1–4 carbon atoms, for example methoxy, and/or by trifluoromethyl.

Acyl can be aliphatic or aromatic acyl groups. The aliphatic acyl has 1–7 carbon atoms, for example 1–4 carbon atoms, such as, formyl, acetyl, propionyl, butyryl, hexanoyl, acryloyl, crotonoyl, propioloyl, which can be substituted further, for example by halogen, such as chlorine, bromine, fluorine, by amino, and/or by alkylamino having 1–4 carbon atoms, such as methyl- or ethylamino groups. Aromatic acyl can, for example, be benzoyl or naphthoyl, which can also be substituted further, for example by halogen, such as chlorine, bromine, fluorine, by alkyl having 1–4 carbon atoms, for example methyl, by hydroxyl, by amino groups, such as, example ethylamino, or by alkoxy groups having 1–7 carbon atoms, such as 1–4 carbon atoms, for example methoxy.

The sugar ($R_1R_7$) is a monosaccharide (n=1) or a disaccharide (n=2), where two monosaccharides are linked glycosidically. The monosaccharide can be a hexose ($C_6H_{12}O_6$), for example an aldohexose, such as, D-(+)-glucose, D-(+)-mannose or D-(+)-galactose. The monosaccharide can be mono-, di- or tri-substituted, independently of one another, by H, OH, $NH_2$, NH(alkyl), N(alkyl)$_2$, alkyl and alkoxy, where the H and/or OH of the monosaccharide can be optionally replaced by substituents. The term "sugar", as used herein, includes amino sugars. An amino sugar is a monosaccharide or disaccharide optionally substituted as described wherein at least one OH- or H-group of the mono- or disaccharide is replaced by an amino group such as $NH_2$, NH(alkyl) or N(alkyl)$_2$.

In one embodiment, m is 1.

$R_7$ may be an aminosugar group of formula (II)

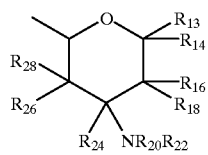

II wherein $R_{13}$, $R_{14}$, $R_{16}$, $R_{18}$, $R_{20}$, $R_{22}$, $R_{24}$, $R_{26}$ and $R_{28}$, are each independently chosen from H, OH, $NH_2$, NHalkyl, N(alkyl)$_2$ and alkoxy, where alkyl and alkoxy have from 1 to 4 carbon atoms.

Examples of $C_1$–$C_4$-alkyl are, for example, methyl, ethyl, propyl, isobutyl and butyl, in particular methyl, and examples of $C_1$–$C_4$-alkoxy are, for example, methoxy, ethoxy, isopropoxy or butoxy, in particular methoxy.

$R_7$ can be an aminosugar of formula (IIA):

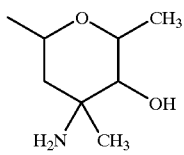

IIA $R_1$ may also be an aminosugar. In one embodiment, n is 2.

$R_1$ may be a group of formula (III)

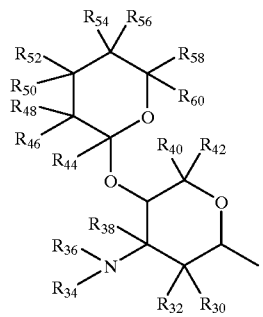

III wherein $R_{30}$ to $R_{60}$, independently of one another, are H, OH, $NH_2$, NHalkyl, N(alkyl)$_2$, or alkoxy, wherein alkyl is a $C_1$–$C_4$ group, such as, methyl, ethyl, propyl, isobutyl and butyl, in particular methyl, and O-alkyl is $C_1$–$C_4$-alkoxy, for example, methoxy, ethoxy, isopropoxy or butoxy, in particular methoxy.

$R_1$ in one embodiment, had the formula (IIIA)

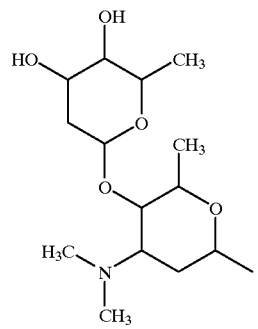

IIIA $R_3$ can be an epoxide-comprising group. The epoxide-comprising group can be a straight-chain or branched alkyl or alkenyl group having from 2 to 12 carbon atoms, such as from 2 to 6 carbon atoms, which comprise one or two epoxide rings (oxiranes). Possible examples are:

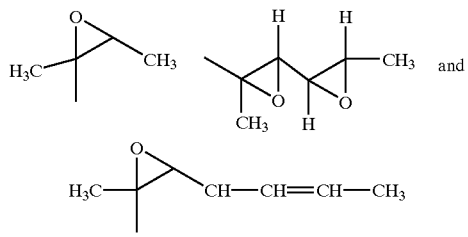

Other than an epoxide-comprising group, $R_3$ can be a straight-chain or branched alkyl having from 1 to 12 carbon atoms, such as 1 to 6 carbon atoms, such as, for example, methyl, ethyl, isopropyl, tert-butyl, hexyl, and also, for example, octyl, dodecyl, or a straight-chain or branched alkenyl having from 2 to 12 carbon atoms, such as 2 to 6 carbon atoms, for example, allyl, crotyl, pentenyl, and also dodecenyl, where these alkyl or alkenyl groups can also be mono- or polysubstituted, for example by hydroxyl.

The invention accordingly relates to pluraflavin A of formula (IA)

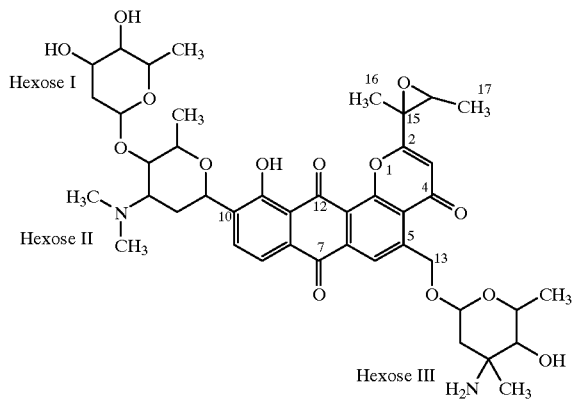

to pluraflavin B of formula (IB)

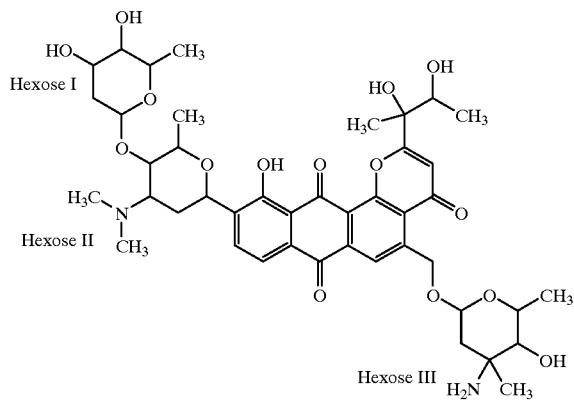

and to pluraflavin E of formula (IE)

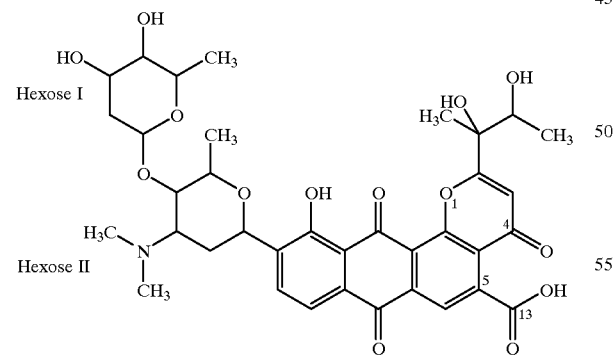

wherein hexose I is a 2,6-dideoxyaldohexose;
hexose II is a 2,3,6-trideoxy-3-dimethylaminohexose and hexose III is a 2,3,6-trideoxy-3-amino-3-methylaldohexose, in all their stereochemical forms and mixtures of these forms in any ratio, and their physiologically acceptable salts and derivatives.

In one embodiment, the compounds are chosen from formulae (IA), (IB) and (IE), wherein
hexose I is oliose,
hexose II is rhodosamine and
hexose III is 3-epi-vancosamine.

According to the invention, the compounds of formula I are obtainable by cultivation, for example by fermentation, of the Actinomycetales species HAG 003959, DSM 12931, or its variants or mutants, under suitable conditions in a culture medium, until at least one of the pluraflavins of formula (IA), (IB) and/or (IE) is present in the culture medium. The pluraflavins may be subsequently isolated from the culture medium and purified and, if appropriate, converted into derivatives and/or into their physiologically acceptable salts.

The invention furthermore relates to a process for preparing a compound of formula I which comprises cultivating, for example by fermenting, the microorganism Actinomycetales species HAG 003959, DSM 12931, or its variants or mutants, under suitable conditions in a culture medium, until at least one of the pluraflavins of formula (IA), (IB) and/or (IE) is present in the culture medium, isolating at least one of the pluraflavins from the culture medium and, if appropriate, converting into derivatives and/or physiologically acceptable salts.

The strain HAG 003959, DSM 12931, its mutants and/or variants are in one embodiment, cultivated in a nutrient solution (also referred to as culture medium) comprising at least one source of carbon atoms and at least one source of nitrogen atoms and the customary inorganic salts, until at least one novel pluraflavin is present in the culture medium; the pluraflavins may be subsequently isolated from the culture medium and, if appropriate, separated into the individual active components.

The cultivation can be carried out under aerobic conditions. The cultivation can be carried out at a temperature ranging from 18 to 35° C. and at a pH ranging from 6 to 8.

In the literature, a large number of reactions for chemical derivatization of quinones have been described. Accordingly, the derivatization of the quinone forms of the present compounds can be carried out using chemical reactions which are known per se. A reduction to the hydroquinone forms of the compounds can, for example, be achieved catalytically with hydrogen, or with metal hydrides, such as aluminum hydrides or boron hydrides. A further suitable example is the conversion of quinones with hydroxylamine or with its derivatives into oximes which for their part can be further chemically converted.

The invention accordingly relates to a compound of formula (IV):

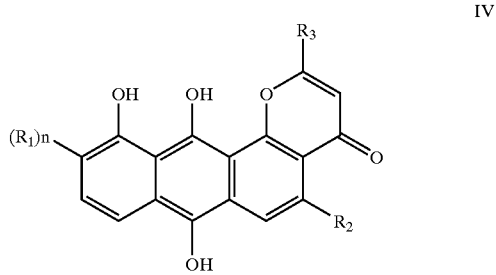

wherein $R_1$, $R_2$, $R_3$ and n are as defined above, in any of its stereochemical forms and mixtures of these forms in any ratio, and a physiologically acceptable salt or derivative thereof.

The pluraflavin derivatives of formulae (IVA), (IVB) and (IVE) (below), are derived from the pluraflavins of formulae (IA), (IB) and (IE), respectively, and they also form part of this invention.

The invention furthermore relates to: a compound of formula (IVA)

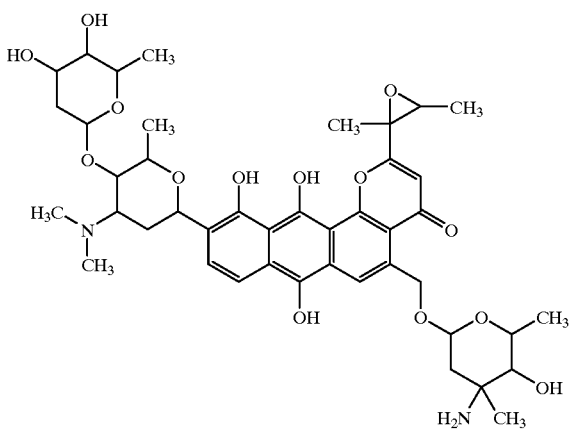

a compound of formula (IVB)

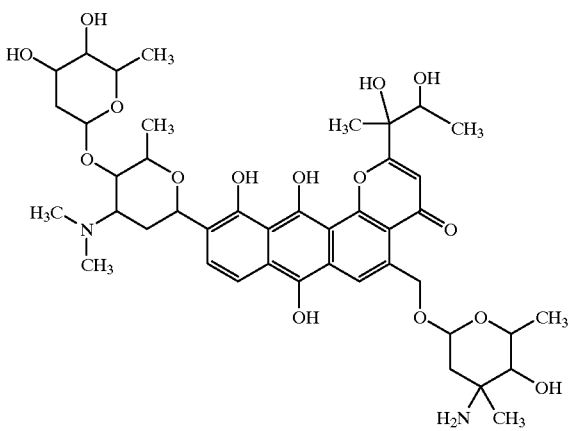

and a compound of formula (IVE)

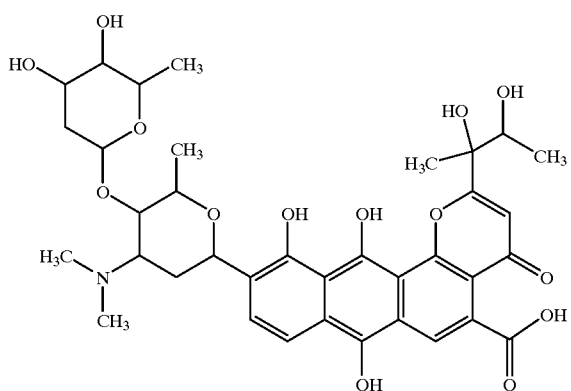

in any of their stereochemical forms and mixtures of these forms in any ratio, and a physiologically acceptable salt or derivative thereof.

Hereinbelow, the invention is described in detail, for example in at least one embodiment.

The pluraflavins according to the invention are produced by Actinomycetales species, in one embodiment, by Actinomycetales spec HAG 003959, DSM 12931. The Actinomycetales species HAG 003959, DSM 12931, has a beigered mycelium and can be identified by conidiophores which are typical for actinomycetes.

A taxonomic examination of the microorganism Actinomycetales spec HAG 003959, DSM 12931, gave the following result of the determination of the strain: the diagnostically important fatty acid analysis by gas chromatography showed high proportions of:

Anteiso 15:0 fatty acid,
Iso 16:0 fatty acid (isopalmitic acid),
Iso 17:0 fatty acid (isomargaric acid),
Anteiso 17:0 fatty acid (anteisomargaric acid) and
cis[9] 18:1 fatty acid (oleic acid), in addition to lower concentrations of other fatty acids.

This fatty acid composition profile permits Actinomycetales $HAG_{13}$ 003959 (DSM 12931) to be assigned taxonomically to the genus Saccharothrix.

An isolate of the microorganism was deposited at the Deutschen Sammlung von Mikroorganismen und Zelikulturen GmbH, MascheroderWeg 1B, D 38124 Braunschweig, Germany, according to the rules of the Budapest Convention on Jul. 16, 1999 under the following number: Actinomycetales species HAG 003959, DSM 12931.

Instead of the strain Actinomycetales species HAG 003959, DSM 12931, it is also possible to use its mutants and variants which synthesize at least one compounds of the pluraflavins according to the invention. Such mutants can be produced in a manner known per se by physical means, for example irradiation, e.g. with ultraviolet or X-rays, or chemical mutagens, such as, for example, ethyl methanesulfonate (EMS), 2-hydroxy-4-methoxybenzophenone (MOB) or N-methyl-N'-nitro-N-nitrosoguanidine (MNNG).

The process according to the invention can be used for fermentation on a laboratory scale (milliliter to liter range) or on an industrial scale (cubic meter scale). Unless indicated otherwise, all percentages are based on weight. In the case of liquids, mixing ratios are based on the volume, unless stated otherwise.

In one embodiment, sources of carbon atoms for aerobic fermentation are assimilable carbohydrates and sugar alcohols, such as glucose, lactose, sucrose or D-mannitol, and hydrocarbon-comprising natural products, such as, for example, malt extract. Suitable sources of nitrogen atoms for cultivation are: amino acids, peptides and proteins and their degradation products, such as peptones or tryptones, furthermore meat extracts, yeast extracts, ground seeds, for example of maize, wheat, beans, soya or cotton, distillation residues of alcohol production, meat meals or yeast extracts, but also ammonium salts and nitrates. Inorganic salts contained in the nutrient solution can, for example, be chlorides, carbonates, sulfates or phosphates of the alkali metals or alkaline earth metals, iron, zinc, cobalt and manganese.

The formation of the pluraflavins according to the invention proceeds in a culture medium which comprises about 0.1 to 5%, such as 0.3 to 2%, of glucose and 0.2 to 5%, such as 0.5 to 3%, of soya meal and 0.05 to 2%, such as 0.2 to 1.0 g/l of corn steep and 0.05 to 1.0 g/l, such as 0.1 to 0.5%, of calcium carbonate and 0.05 to 1.0 g/l, such as 0.1 to 1.0 g/l, of sodium chloride. The percentages are in each case based on the weight of the entire culture medium.

In the culture medium, Actinomycetales species HAG 003959, DSM 12931, produces a mixture of pluraflavins. Depending on the composition of the culture medium, the proportion of at least one of the pluraflavins according to the invention may vary. Furthermore, via the composition of the medium, it is possible to control the synthesis of individual pluraflavins, so that one or even more of the pluraflavins are not produced at all by the microorganism, or in an amount below the detection limit.

In one embodiment, the culture comprises one detectable pluraflavin. In further embodiments the pluraflavins A, B or E are formed.

In addition to the pluraflavins A, B and E (compounds of formula (IA), (IB) and (IE), respectively), other related compounds, which differ from the compounds represented in the formulae (IA), (IB) and (IE) in that they are glycosylated differently, are also formed in the culture medium of Actinomycetales species HAG 003959, DSM 12931. Thus, as by-product, a further pluraflavin (pluraflavin C) with a molecular weight of 974 Da and a degradation product of pluraflavin A, molecular weight 692.77, $C_{37}H_{44}N_2O_{11}$, were detected. In the latter compound, hexose I is missing; under acidic conditions, the 2,6-dideoxyaldohexose can be hydrolytically cleaved off from pluraflavin A.

The microorganism is cultivated aerobically, i.e., for example, submersed with shaking or stirring in shaker flasks or fermenters, if appropriate with introduction of air or oxygen. It can be carried out in a temperature range from approximately 18 to 35° C., such as from approximately 25 to 32° C., including from 27 to 30° C. The pH generally should range from 6 to 8, such as from 6.5 to 7.5. Under these conditions, the microorganism is generally cultivated over a period ranging from 24 to 300 hours, such as from 36 to 140 hours.

Cultivation is advantageously carried out in several stages, i.e. at least one preculture is first prepared in a liquid nutrient medium, which is then inoculated into the actual production medium, the main culture, for example in the volume ratio 1:10. The preculture is obtained, for example, by inoculating a mycelium into a nutrient solution and allowing it to grow for approximately 36 to 120 hours, such as for 48 to 96 hours. The mycelium can be obtained, for example, by allowing the strain to grow for about 3 to 40 days, such as for 4 to 10 days, on a solid or liquid nutrient medium, for example malt-yeast agar or oatmeal agar.

The progress of the fermentation can be monitored by the pH of the cultures or the mycelium volume, and also by chromatographic methods, such as, for example, thin-layer chromatography or high pressure liquid chromatography or testing the biological activity. The pluraflavins according to the invention may be found in both the mycelium and in the culture filtrate. The isolation process described below generally serves to purify the pluraflavins according to the invention, such as to purify the pluraflavins A, B and E.

Isolation and/or purification of the pluraflavins according to the invention from the culture medium is carried out by known methods, taking into account the chemical, physical and biological properties of the natural products. To test the pluraflavin concentration in the culture medium or in the individual isolation stages, it is possible to use thin-layer chromatography, for example on silica gel using chloroform/methanol/-glacial acetic acid/water mixtures (for example in the ratio 8:1:1:0.2) as mobile phase, or HPLC. In the thin-layer chromatographic separation, detection can be carried out, for example, using staining reagents, such as a-naphthol/sulfuric acid, where the amount of the substance formed is expediently compared to a calibration solution.

According to the invention, pluraflavins may be isolated from either mycelium or culture medium. Generally, the mycelium is initially separated off from the culture medium by the customary methods, and the pluraflavins are subsequently extracted from the cell material using an optionally water-miscible organic solvent. The organic-solvent phase contains pluraflavins according to the invention; if appropriate, they are concentrated under reduced pressure and purified further as described below.

If appropriate, the culture filtrate is combined with the concentrate of the mycelium extract and extracted with a suitable water-immiscible organic solvent, for example with n-butanol. The organic phase is then separated off and, if appropriate, concentrated under reduced pressure. To defat the product of value, the concentrate can be diluted with an nonpolar solvent wherein the pluraflavins according to the invention are only sparingly soluble, such as, for example, with hexane, petroleum ether, diethyl ether. This causes the pluraflavins to precipitate, and the lipophilic impurities remain dissolved and are removed by customary solid-liquid phase separation. The precipitate, which contains all pluraflavins to be isolated, is dissolved in 1/30 of the original volume of water/methanol. The precipitate is dissolved completely and is lyophilized. The lyophilizate, which is referred to as crude product hereinbelow, comprises 0.5 to 50% of pluraflavin and is used for further isolation.

The further purification of one or more of the pluraflavins according to the invention is carried out by chromatography on suitable materials, such as on molecular sieves, on normal phase carriers, such as, for example, silica gel, alumina, on ion exchangers or on adsorber resins and/or on reversed phase mediums (RP). With the aid of this chromatography, the pluraflavins are separated. The chromatography of the pluraflavins is carried out using buffered aqueous solutions or mixtures of aqueous and organic solutions.

Mixtures of aqueous or organic solutions are understood as meaning all water-miscible organic solvents, such as methanol, propanol and acetonitrile, in a concentration ranging from 10 to 80% solvent, for example from 40 to 60% solvent, or else all buffered aqueous solutions which are miscible with organic solvents. The buffers to be used may be the same as indicated above.

Separation of the pluraflavins based on their differing polarity may be carried out with the aid of reversed phase chromatography, for example on MCI® (adsorber resin from Mitsubishi, Japan) or Amberlite XAD® (TOSOHAAS), on further hydrophobic materials, such as, for example, on RP-8 or RP-18 phases. Moreover, separation can be carried out with the aid of normal phase chromatography, for example on silica gel, alumina and the like.

The chromatography of the pluraflavins may be carried out using buffered or acidified aqueous solutions or mixtures of aqueous solutions with alcohols or other water-miscible organic solvents. The organic solvent used can be propanol and acetonitrile.

Buffered or acidified aqueous solutions are understood as meaning, for example, water, phosphate buffer, ammonium acetate, citrate buffer in a concentration from 1 mM to 0.5 M, and also formic acid, acetic acid, trifluoroacetic acid or all commercial acids known to the person skilled in the art, for example, in a concentration ranging from 0.01 to 3%, such as from 0.1%.

Chromatography can be carried out using a gradient starting with 100% aqueous buffer and ending with 100% solvent; for example a linear gradient ranging from 10 to 50% using 2-propanol or acetonitrile.

Alternatively, it is also possible to carry out gel chromatography or chromatography on hydrophobic phases.

Gel chromatography can be carried out on polyacrylamide or mixed polymer gels, such as, for example, Biogel-P 2®

(Biorad), Fractogel TSK HW 40® (Merck, Germany or Toso Haas, USA) or on Sephadex® (Pharmacia, Uppsala, Sweden).

The order of the chromatographies mentioned above can be reversed.

A further, highly effective purification step for pluraflavins is crystallization. The pluraflavins crystallize from solutions in organic solvents and from mixtures of water with organic solvents. Crystallization can be carried out in a manner known per se, for example by concentration or cooling of saturated pluraflavin solutions.

The pluraflavins according to the invention are stable in the solid state and in solutions having a pH ranging from 3 to 8, for example frompH 4 to 6, and they can therefore be incorporated into customary pharmaceutical preparations.

The pluraflavins of formula (I) and the derivatives derived therefrom can be converted by methods known to the person skilled in the art into the corresponding physiologically acceptable salts.

Physiologically acceptable salts of compounds of formula (I) are understood as meaning both their organic and inorganic salts, such as are described in Remington's Pharmaceutical Sciences (17th edition, page 1418 (1985)). Based on the physical and chemical stability and the solubility, sodium, potassium, calcium and ammonium salts, inter alia, are possible embodiments of acidic groups; salts of hydrochloric acid, sulfuric acid, phosphoric acid or of carboxylic acids or sulfonic acids, such as, for example, acetic acid, citric acid, benzoic acid, maleic acid, fumaric acid, tartaric acid and p-toluenesulfonic acid, inter alia, are possible embodiments of basic groups.

The invention furthermore embraces chemical equivalents, herein also referred to as "derivatives", of the compounds of formula (I) which have the same or substantially the same activity or which can be converted into the compound according to the invention. The equivalents mentioned include, for example, esters and ethers, complexes and also reduction products of the compounds according to the invention.

Esters and ether derivatives and reduction products can be prepared by processes described in the literature, for example in "Advanced Organic Synthesis", $4^{th}$ edition, J. March, John Wiley & Sons, 1992. The carboxy group (formula IE, IVE) and hydroxy groups of the compounds of the formula (I) can be converted to an ester, such as $C_1$–$C_4$ alkyl ester, or ether group, for example, acetals and ketals of the hydroxy groups.

Stable complexes of the compounds of the formula (I) may be formed with physiologically acceptable inorganic cations, such as calcium or magnesium.

The present invention embraces all stereoisomeric forms of the compounds of formula (I). Centers of asymmetry of the compounds of formulae (IA), (IB) and (IE) can, independently of one another, in each case may have the S configuration or the R configuration. The oxiranes of the epoxide-comprising group can be in any position; for example, oxiranes which incorporate the carbon atoms 2' and 3'. The invention includes all possible enantiomers and diastereomers, and also mixtures of at least two stereoisomeric forms, for example mixtures of enantiomers and/or diastereomers, in any ratio. Thus, the invention provides enantiomers in enantiomerically pure form, both as laevorotatory and as dextrorotatory antipodes, R and S configurations, in the form of racemates and in the form of mixtures of the two enantiomers in any ratio. If there is a cis/trans isomerism, the invention provides both the cis form and the trans form and mixtures of these forms in any ratio.

On account of their useful pharmacological properties, the compounds according to the invention are suitable for use as pharmaceuticals in human and/or veterinary medicine. They have antibiotic activity and, in addition to the antibacterial action, antimycotic, i.e. fungi-inhibiting, including phytopathogenic fungi, antiprotozoic and antiparasitic properties.

The compounds according to the invention can be used for cancerous diseases, for example as chemotherapeutics. Owing to their cytostatic properties, such as their potent antitumor activity, and an antimicrobial action, they can be used, for example, as cytostatics for malignant degenerations in animals and humans.

In the case of tumor cells which have developed resistances to conventional agents, only novel agents have a therapeutically adequate effect. Thus, the pluraflavins according to the invention and derivatives thereof of formula (I) have a potentially excellent activity even against these problem cell types.

The invention also relates to pharmaceutical preparations which comprise at least one of the pluraflavins according to the invention and/or derivatives thereof. Plurflavins may be used in a mixture with at least one suitable auxiliary or excipient. The excipients used for humans can be all pharmacologically acceptable excipients and/or auxiliaries.

The invention also relates to a process for preparing a pharmaceutical according to the invention which comprises bringing at least one compound according to the invention into a suitable administration form using a pharmaceutically suitable and physiologically acceptable excipient and, if appropriate, further suitable active compounds, additives or auxiliaries.

The pharmaceuticals according to the invention are generally administered orally, topically or parenterally, but rectal administration is also possible. Suitable solid or liquid pharmaceutical preparation forms are, for example, granules, powders, tablets, coated tablets, (micro)capsules, suppositories, syrups, emulsions, suspensions, aerosols, drops or injectable solutions in ampoule form, and preparations having a protracted release of active compound, in whose preparation excipients and additives and/or auxiliaries, such as disintegrants, binders, coating agents, swelling agents, glidants or lubricants, flavorings, sweeteners or solubilizers are customarily used. Frequently used excipients or auxiliaries which may be mentioned are, for example, magnesium carbonate, titanium dioxide, lactose, mannitol and other sugars, talc, lactoprotein, gelatin, starch, vitamins, cellulose and its derivatives, animal or vegetable oils, polyethylene glycols and solvents such as, for example, sterile water, alcohols, glycerol and polyhydric alcohols.

If appropriate, the dose units can be microencapsulated for oral administration to delay the release or to extend the release over a relatively long period of time, such as, for example, by coating or embedding the particulate active compound into suitable polymers, waxes or the like.

The pharmaceutical preparations may be produced and administered in dose units, each unit comprising as active ingredient a certain dose of at least one compound of the pluraflavins according to the invention and/or derivatives thereof. In the case of solid dose units such as tablets, capsules and suppositories, this dose can be up to approximately 200 mg, but can be approximately 0.1 to 100 mg, and in the case of solutions for injection in ampoule form up to about 200 mg, but can be about 0.1 to 100 mg, per day.

The daily dose to be administered depends on the bodyweight, age, sex and condition of the mammalian subject. However, higher or lower daily doses may also be called for. The daily dose can either be administered by being given on one occasion in the form of a single dose unit or in the form of several smaller dose units, or else being given on several occasions, at predetermined intervals, in the form of subdivided doses.

The invention is illustrated further in the examples which follow. Percentages are based on weight. In the case of liquids, mixing ratios are based on volume, unless stated otherwise.

The following are illustrative examples of the present invention but not limitative of the scope thereof.

EXAMPLES

Example 1

Preparation of a glycerol culture of Actinomycetales species HAG 003959, DSM 12931.

100 ml of nutrient solution (malt extract 2.0%, yeast extract 0.2%, glucose 1.0%, $(NH_4)_2HPO_4$ 0.05%, pH 6.0) in a sterile 300 ml Erlenmeyer flask was inoculated with the strain Actinomycetales species HAG 003959, DSM 12931, and incubated on a rotating shaker at 28° C. and 180 rpm for 7 days. 1.5 ml of this culture was then diluted with 1.5 ml of 99% strength glycerol and stored at −20° C.

Example 2

Preparation of a culture or a preculture in an Erlenmeyer flask of Actinomycetales species HAG 003959, DSM 12931

A sterile 300 ml Erlenmeyer flask which contained 100 ml of the following nutrient solution: 15 g of glucose/l, 15 g of soya meal/l, 5 g of corn steep/l, 2 g of $CaCO_3$/l and 5 g of NaCl/l was inoculated with a culture grown on an oblique tube (same nutrient solution, but with 2% agar) or with 1 ml of a glycerol culture (see Example 1) and incubated on a shaker at 180 rpm and 30° C. The maximum production of at least one compound of the pluraflavins according to the invention was reached after about 120 hours. For inoculating 10 and 200 l fermenters, a 48- to 96-hour old submersed culture (amount for inoculation about 10%) from the same nutrient solution was sufficient.

Example 3

Preparation of the pluraflavins

A 9 fermenter was operated under the following conditions:

| | |
|---|---|
| Nutrient medium: | 15 g of glucose/l; |
| | 15 g of soya meal/l; |
| | 5 g of corn steep, solid/l; |
| | 2 g of $CaCO_3$/l; |
| | 5 g of NaCl/l; |
| | pH 7.0 (prior to sterilization) |
| Duration of the process: | 92 hours |
| Incubation temperature: | 28° C. |
| Stirrer speed: | 300 rpm |
| Aeration: | 5 l min$^{-1}$ |

By repeated addition of ethanolic polyol solution, it was possible to optionally suppress the formation of foam. The production maximum was reached after about 70 to 96 hours.

Example 4 isolation of the pluraflavin mixture from the culture solution of Actinomycetales species HAG 003959, DSM 12931.

After the fermentation of Actinomycetales species HAG 003959, DSM 12931, ended, the culture broth of the fermenter, obtained according to Example 3 (90 liters), was filtered with the addition of about 2% filter aid (for example Celite®), and the cell material (0.6 liter) was extracted with 3 liters of methanol. The active-compound-containing methanolic solution was freed from mycelium by filtration and concentrated under reduced pressure. The concentrate was, together with the culture filtrate (7 liters), applied to a prepared 0.4 liter ®MCI GEL, CHP20P column. Elution was carried out using a gradient of 0.1% acetic acid in water to 0.1% acetic acid in 2-propanol. The column flow-through (1.2 liters per hour) was collected in fractions (of 0.25 liter each) and the pluraflavin-containing fractions (20 to 23) were pooled. Concentration under reduced pressure and freeze-drying gave 1.4 g of a brown powder.

Example 5

Enrichment of the pluraflavin components by gel chromatography.

1.4 g of the product obtained according to Example 4 was applied to a column with a capacity of 3.9 liters (width× height=10 cm×50 cm) filled with Fractogel® TSK HW-40 s. The mobile phase water/acetonitrile (1:1) was pumped through the column at a flow rate of 50 ml per minute, and the column flow-through was collected in fractions (65 ml). The pluraflavins were mainly in fractions 13 to 16. They were pooled and freed from the solvent under reduced pressure. They gave 130 mg of pluraflavin mixture.

Example 6

Separation of the pluraflavin components on reverse phase RP-18.

A preparative HPLC column with a capacity of 122 ml (1.25 cm (ID)×25 cm H) was filled with ®Nucleosil 100-7 C18 HD, and the 130 mg of the pluraflavin mixture obtained according to Example 5 was applied. Elution was carried out using 10% acetonitrile and 0.1 M aqueous ammonium acetate solution. The column flow-through was 50 ml/minute, and fractions of in each case 50 ml content were collected. Fraction 6 comprised the pluraflavin E, the pluraflavin C was in fractions 12–17, the pluraflavin B was in fractions 25 to 27 and the pluraflavin A was in fractions 35 to 37. After concentration under reduced pressure and freeze-drying, the following amounts were obtained:

pluraflavin A: 22 mg, ESI+MS: 823 Da $(M+H)^+$, pluraflavin B: 18 mg, ESI+MS: 841 Da $(M+H)^+$, pluraflavin C: 11 mg, ESI+MS: 974 Da $(M+H)^+$, pluraflavin E: 5 mg, ESI+MS: 712 Da $(M+H)^+$.

Example 7

Final purification of pluraflavin A and conversion into the trifluoroacetate salt form.

The fractions 35 to 37, obtained according to Example 6, were, after freeze-drying (22 mg), dissolved in 10% acetonitrile in water, adjusted to pH 2.8 with trifluoroacetic acid and applied to a 250/10 LiChrospher RP-18e (5 $\mu$m)® column. Elution was carried out using 0.05% aqueous trifluoroacetic acid in 11 to 22% acetonitrile. Concentration under reduced pressure and freeze-drying gave 18 mg of pluraflavin A-trifluoroacetate salt.

Example 8

Identification of pluraflavin A.

Appearance: a deep-yellow substance which was soluble in polar organic solvents but only sparingly soluble in water. The acid addition salts are water-soluble. The compound was stable in neutral and mildly acidic medium, but unstable in the alkaline and strongly acidic range. UV-Maxima: 214, 243, 270 (Sh), 290 (Sh), 426 nm in water/acetonitrile (8:2), pH 2 and 214, 243, 270 (Sh), 290 (Sh) and 426 nm in water/acetonitrile (6:4), pH 7. IR bands: 3424, 1680,1600, 1464, 1427, 1300, 1203, 1131, 1066, 1009, 801, 721 cm$^{-1}$. By high resolution mass spectometry, the following molecular weight was found for $(M+H)^+$:823.370631 Da, corresponding to the empirical formula for pluraflavin A of $C_{43}H_{54}N_2O_{14}$. Electron spray ionization (ESI, positive) gives, via MS/MS fragmentation, the following ions: 823, 693, 680, 550, 480, 390, 320, 144 and 131 Da. NMR signals: see Table 1.

TABLE 1

¹H and ¹³C chemical shifts of
pluraflavin A in methanol-d₄ and DMSO-d₆
at 300° K.

| position | methanol-d₄ ¹³C δ(ppm) | methanol-d₄ ¹H δ(ppm) | DMSO-d₆ ¹³C δ(ppm) | DMSO-d₆ ¹H δ(ppm) |
|---|---|---|---|---|
| 2 | 168.39 | — | 165.62 | — |
| 3 | 111.95 | 6.37 s | 110.39 | 6.27 s |
| 4 | 180.25 | — | 177.56 | — |
| 4a | 126.08 | — | 124.33 | — |
| 5 | 150.44 | — | 148.22 | — |
| 6 | 121.34 | 8.61 s | 119.05 | 8.43 s |
| 6a | 138.34 | — | 136.28 | — |
| 7 | 182.68 | — | 181.12 | — |
| 7a | 133.23 | — | 131.18 | — |
| 8 | 120.05 | 7.86 d | 118.29 | 7.78 d |
| 9 | 135.63 | 7.90 d | 134.41 | 7.87 d |
| 10 | 137.35 | — | 135.79 | — |
| 11 | 161.06 | — | 159.39 | — |
| 11-OH | — | — | — | 13.38 s, brd |
| 11a | 118.14 | — | 116.43 | — |
| 12 | 189.12 | — | 187.39 | — |
| 12a | 122.00 | — | 120.35 | — |
| 12b | 157.66 | — | 155.50 | — |
| 13 | 70.83 | 5.38 d, 5.63 d | 68.48 | 5.30 d, 5.51 d |
| 14 | 61.17 | — | 59.35 | — |
| 15 | 63.69 | 3.41 q | 61.61 | 3.48 q |
| 16 | 20.24 | 1.92 s | 19.32 | 1.86 s |
| 17 | 13.69 | 1.27 d | 12.93 | 1.22 d |
| 1' | 98.90 | 5.04 dd | 96.57 | 5.06 d, brd |
| 2' | 37.24 | 2.05, 2.12 | 35.50 | 1.87, 1.95 |
| 3' | 58.32 | — | 56.33 | — |
| 3'Me | 24.57 | 1.50 s | | 1.35 s |
| 3'NH₂ | — | — | | 8.16 s, brd |
| 4' | 71.15 | 3.27 s, brd | 68.65 | 3.17 d |
| 4'-OH | — | — | | 5.47 d |
| 5' | 70.44 | 4.00 q | 68.19 | 4.01 q |
| 6' | 17.21 | 1.34 d | 16.75 | 1.18 d |
| 1" | 70.23 | 5.51 t | 68.21 | 5.44 brd |
| 2" | 28.00 brd | 2.48 m, 2.91 m, brd | | 2.35 brd, 2.78 brd |
| 3" | 65.19 | 3.45 m, brd | 62.19 | 3.43 brd |
| 3"NMe | 43.24 brd, 41.65 brd | 3.05 brd, 3.05 brd | 42.14, 39.25 | 2.89, 2.97 |
| 3"NH⁺ | — | — | — | 8.78 brd |
| 4" | 75.13 | 4.32 s, brd | 71.88 | 4.20 s, brd |
| 5" | 72.55 | 3.97 q, brd | 70.22 | 3.75 q, brd |
| 6" | 18.09 | 1.40 d | 17.54 | 1.28 d |
| 1''' | 101.39 | 5.24 m, brd | 98.89 | 5.11 brd |
| 2''' | 33.40 | 2.05, 2.10 | 32.07 | 1.75, 1.92 |
| 3''' | 66.61 | 4.12 m | 64.17 | 3.96 m, brd |
| 3'''-OH | — | — | | 4.70 s, brd |
| 4''' | 71.98 | 3.67 | 70.13 | 3.45 brd |
| 4'''-OH | — | — | | 4.44 s, brd |
| 5''' | 69.52 | 4.16 q, brd | 67.05 | 4.10 q, brd |
| 6''' | 17.51 | 1.28 d | 16.94 | 1.10 d |

For the aldohexose III, the observed NOEs were consistent with a relative SRSS or RSRR stereochemistry at the chiral centers 1', 3', 4', 5' (see H-III). This corresponds to the C-3 epimer of vancosamine.

H-III. Relative stereochemistry of hexose III.

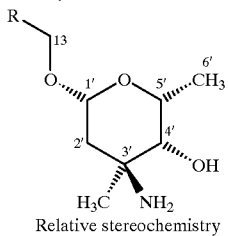

Relative stereochemistry

The NOE effects observed for the hexose II favor the relative stereochemistry RSSS or SRRR for the chiral centers 1",3", 4", 5" (see H-II).

H-II. Relative stereochemistry of hexose II.

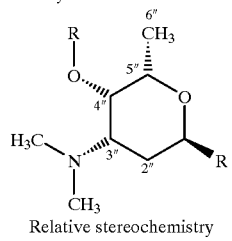

Relative stereochemistry

The same relative stereochemistry (RSSS, SRRR) for the asymmetric carbon atoms 1''', 3''', 4''', 5''' was consistent with the detected NOEs of hexose I (see H-I).

H-I. Relative stereochemistry of hexose I.

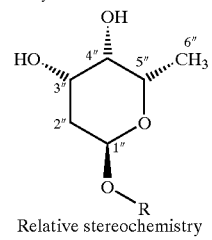

Relative stereochemistry

Example 9

Identification of pluraflavin B.

Appearance:
deep-yellow substance which was soluble in polar organic solvents, but only sparingly soluble in water. The acid addition salts are water-soluble. The compound was stable in neutral and mildly acidic medium, but unstable in the alkaline range.

UV maxima: 214, 243, 270 (Sh), 290 (Sh), 426 nm in water/acetonitrile (8:2), pH 2 and 214, 243, 270 (Sh), 290 (Sh) and 426 nm in water/acetonitrile (6:4), pH 7.

Pluraflavin B has the empirical formula $C_{43}H_{56}N_2O_{15}$, the molecular weight was 840.9 Da.

NMR signals: see Table 2.

TABLE 2

$^1H$ and $^{13}C$ chemical shifts of pluraflavin B in methano-$d_4$ and comparison with pluraflavin A at 300° K.

| | Pluraflavin B (methanol-$d_4$) | | pluraflavin A (methanol-$d_4$) | |
|---|---|---|---|---|
| position | $^{13}C$ δ(ppm) | $^1H$ δ(ppm) | $^{13}C$ δ(ppm) | $^1H$ δ(ppm) |
| 2 | 176.38 | — | 168.39 | — |
| 3 | 111.10 | 6.73 s | 111.95 | 6.37 s |
| 4 | 181.26 | — | 180.25 | — |
| 4a | 125.96 | — | 126.08 | — |
| 5 | 150.43 | — | 150.44 | — |
| 6 | 121.03 | 8.52 s | 121.34 | 8.61 s |
| 6a | 138.12 | — | 138.34 | — |
| 7 | 182.66 | — | 182.68 | — |
| 7a | 133.16 | — | 133.23 | — |
| 8 | 120.04 | 7.81 d | 120.05 | 7.86 d |
| 9 | 135.52 | 7.83 d | 135.63 | 7.90 d |
| 10 | 137.44 | — | 137.35 | — |
| 11 | 161.02 | — | 161.06 | — |
| 11-OH | — | — | — | — |
| 11a | 118.01 | — | 118.14 | — |
| 12 | 189.24 | — | 189.12 | — |
| 12a | 121.89 | — | 122.00 | — |
| 12b | 157.41 | — | 157.66 | — |
| 13 | 70.83 | 5.36 d, 5.60 d | 70.83 | 5.38 d, 5.63 d |
| 14 | 77.67 | — | 61.17 | — |
| 15 | 72.61 | 4.40 q | 63.69 | 3.41 q |
| 16 | 23.90 | 1.67 s | 20.24 | 1.92 s |
| 17 | 17.00 | 1.35 d | 13.69 | 1.27 d |
| 1' | 98.87 | 5.05 dd | 98.90 | 5.04 dd |
| 2' | 37.20 | 2.09 m | 37.24 | 2.05, 2.12 |
| 3' | 58.39 | — | 58.32 | — |
| 3'Me | 24.45 | 1.51 s | 24.57 | 1.50 s |
| 3'$NH_2$ | — | — | — | — |

TABLE 2-continued $^1$H and $^{13}$C chemical shifts of pluraflavin B in methano-d$_4$ and comparison with pluraflavin A at 300° K.

| | Pluraflavin B (methanol-d$_4$) | | pluraflavin A (methanol-d$_4$) | |
|---|---|---|---|---|
| position | $^{13}$C δ(ppm) | $^1$H δ(ppm) | $^{13}$C δ(ppm) | $^1$H δ(ppm) |
| 4' | 71.08 | 3.29 s, brd | 71.15 | 3.27 s, brd |
| 4-OH | — | — | — | — |
| 5' | 70.42 | 4.01 q | 70.44 | 4.00 q |
| 6' | 17.19 | 1.33 d | 17.21 | 1.34 d |
| 1" | 70.13 | 5.48 t | 70.23 | 5.51 t |
| 2" | 27.74 | 2.50 m, 2.88 m | 28.00 brd | 2.48 m, 2.91 m, brd |
| 3" | 65.14 | 3.46 m | 65.19 | 3.45 m, brd |
| 3"NMe | 43.30, 41.40 | 3.01 s, 3.12 s | 43.24 brd, 41.65 brd | 3.05 brd, 3.05 brd |
| 3"NH$^+$ | — | — | — | — |
| 4" | 75.02 | 4.32 s, brd | 75.13 | 4.32 s, brd |
| 5" | 72.61 | 3.97 q, brd | 72.55 | 3.97 q, brd |
| 6" | 18.15 | 1.39 d | 18.09 | 1.40 d |
| 1'" | 101.38 | 5.24 m, brd | 101.39 | 5.24 m, brd |
| 2'" | 33.42 | 2.07 m | 33.40 | 2.05, 2.10 |
| 3'" | 66.59 | 4.13 m | 66.61 | 4.12 m |
| 3'"-OH | — | — | — | — |
| 4'" | 71.97 | 3.67 brd | 71.98 | 3.67 |
| 4'"-OH | — | — | — | — |
| 5'" | 69.52 | 4.16 q, brd | 69.52 | 4.16 q, brd |
| 6'" | 17.49 | 1.27 d | 17.51 | 1.28 d |

Example 10
Final purification of pluraflavin E.

Fraction 6, obtained according to Example 6, was, after freeze-drying (5 mg), dissolved in 10% acetonitrile in water, adjusted to pH 2.8 with trifluoroacetic acid and applied to a 250/10 LiChrospher RP-18e (5 μm)® column. Elution was carried out using 0.05% aqueous trifluoroacetic acid in gradient mode from 11 to 22% of acetonitrile. Concentration under reduced pressure and freeze-drying gives 2.7 mg of pluraflavin E-trifluoroacetate salt.

Example 11
Identification of pluraflavin E.

Appearance: a deep-yellow substance which was soluble in polar organic solvents but only sparingly soluble in water. The acid addition salts are water-soluble. The compound was stable in neutral and mildly acidic medium, but unstable in the alkaline and strongly acidic range. UV-maxima: 213, 244, 270 (Sh), 290 (Sh), 426 nm in water/acetonitrile (8:2), pH 2, and 213, 244, 270 (Sh), 290 (Sh) and 426 nm in water/acetonitrile (6:4), pH 7. The following molecular weight was found by mass spectrometry for (M+H)+: 712 Da, corresponding to the empirical formula $C_{36}H_{41}NO_{14}$ for pluraflavin E.
NMR signals: see Table 3.

TABLE 3

$^1$H and $^{13}$C chemical shifts of pluraflavin E in methanol-d$_4$ at 300° K.

| position | $^{13}$C δ(ppm) | $^1$H δ(ppm) |
|---|---|---|
| 2 | 176.48 | — |
| 3 | 110.30 | 6.69 s |
| 4 | 178.39 | — |
| 4a | 124.69 | — |
| 5 | 149.56 | — |
| 6 | 121.17 | 7.92 s |
| 6a | 138.95 | — |
| 7 | 182.40 | — |
| 7a | 133.21 | — |
| 8 | 119.82 | 7.60 d |
| 9 | 135.61 | 7.74 d |
| 10 | 137.04 | — |
| 11 | 161.33 | — |
| 11-OH | — | — |
| 11a | 118.04 | — |
| 12 | 189.21 | — |
| 12a | 121.59 | — |
| 12b | 156.86 | — |
| 13 | 175.28 | — |
| 14 | 77.69 | — |
| 15 | 72.61 | 4.35 q |
| 16 | 23.78 | 1.62 s |
| 17 | 17.09 | 1.31 d |
| 1" | 70.34 | 5.46 dd |
| 2" | 27.35 | 2.86 m, 2.44 m |
| 3" | 64.88 | 3.50 m |
| 3"NMe | 42.5 brd | 3.08 |
| 3"NH$^+$ | — | — |
| 4" | 75.22 | 4.30 s, brd |
| 5" | 72.29 | 3.87 q, brd |
| 6" | 18.25 | 1.35 d |
| 1'" | 101.40 | 5.23 m |
| 2'" | 33.43 | 2.08 m, 2.06 m |
| 3'" | 66.61 | 4.12 m |
| 3'"-OH | — | — |
| 4'" | 72.03 | 3.67 s, brd |
| 4'"-OH | — | — |
| 5'" | 69.50 | 4.17 q, brd |
| 6'" | 17.52 | 1.28 d |

Example 12
Examination of cytostatic activity.

(a) To determine the cytostatic activity, rat hepatoma cells were used which were obtained from the strain collection American Type Culture Collection under the number ATCC CRL-1548, Jo No.223 and 228 The strain was kept in the "MEM (EAGLE) with Glutamax" medium [GIBCO BRL No.4109-028] with 10% fetal calf serum [GIBCO BRL No. 10270-106] and 10 μl of penicillin-streptomycin [GIBCO BRL No. 15140-114]/ml. 96-well microtiterplates [Greiner, No. 15140-114] were used. Each well was initially charged with 140 μl of culturing nutrient solution and in each case inoculated with 215,000 cells. The plates were then incubated at 37° C. and 5% $CO_2$ for 20–24 hours. A dilution series of pluraflavins with concentrations of 100, 50, 25, 12.5, 6.25, 3.125, 1.5625, 0.7813, 0.3906, 0.195, 0.094, 0.047 and 0 μM, which had been prepared beforehand, was then pipetted in the corresponding order. After a further incubation time of 22 hours at 37° C. in an atmosphere of 5% $CO_2$, the liquid medium was then aspirated. The cells that remained were stained with 100 μl of RPMI 1640 [GIBCO BRL No. 32404-014]/well and 20 μl of Cell Titer 96 Aqueous [PROMEGA No. G5430]/well. Light absorption at 590 nm was measured directly after addition and after 2 hours of incubation, as above. The cytostatic effect was calculated from the change in light absorption.

$IC_{50}$ for pluraflavin A = <50 nM;
$IC_{50}$ for pluraflavin B = <50 nM.

Example 12 (b)

Antiproliferation effects of pluraflavin A and flavopiridol on selected tumor cell lines.

MTT, a water soluble tetrazolium salt, is converted to an insoluble purple formazan when dissolved by cleavage of the tetrazolium ring by dehydrogenase enzymes in active mitochondria. Dead cells do not cause this change. This method was used to quantitate proliferation in order to determine activity of potential chemotherapeutic compounds.

All cells were maintained in RPMI 1640 (Life Technologies, Gaithersburg, Mdi) containing 10% heat-inactivated Fetal Bovine Serum, penicillin /streptomycin and supplemented with L-glutamine.

Cells were plated in 96-well tissue culture plates at the following densities:

| | |
|---|---|
| Breast | 2500 cells/well |
| Prostate | 2600 cells/well |
| Colon | 1000 cells/well |
| Lung | 1000 cells/well |

Cells were allowed to adhere overnight at 37° C., 5% $CO_2$.

Pluraflavin A was diluted in culture mediawlth the final concentration of compound as follows:

50.0, 16.67, 5.56, 1.85, 0.617, 0.206, 0.069, 0.023 μM Flavopiridl was diluted at: 2.0, 0.222, 0.074, 0,025, 0.008, 0.003, 0.001 μM Both compounds were tested in triplicate at all concentrations.

The cells were washed with fresh media and the compounds added to the cells in a final volume of 100 μl. The cells plus compound were allowed to incubate at 37° C., 5% $CO_2$ for approximately 72 hours.

At the desired time point, 25 μl of MTT (10 mg/ml in HBSS) were added to each well. Plates were incubated at 37° C. for 2–4 hours. MTT and media were removed and 200 μl DMSO were added per well. Readings were taken at 570 nm. The results are given below:

| Cells | Pluraflavin A $IC_{50}$ | Flavopiridol $IC_{50}$ |
|---|---|---|
| Breast | <23 nM | 90 nM |
| Prostate | 10 nM | 80 nM |
| Colon | 0.35 nM | 30 nM |
| Lung | 3.0 nM | 90 nM |

In a soft agar assay, pluraflavin A and flavopiridol were tested against leukemia cells. The $IC_{50}$ results were: 60 nM (pluraflavin A) and 0.5, 0.6 μM (flavopiridol),

What is claimed is:

1. A compound of formula I

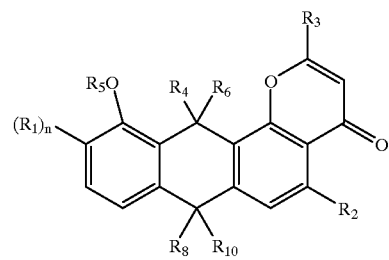

wherein $R_1$ is a sugar group;

$R_2$ is —COOH or —$CH_2$—O—$(R_7)m$, wherein $R_7$ is a sugar group;

$R_3$ is chosen from epoxide-comprising groups, $C_1$–$C_6$-alkyl groups and $C_2$–$C_6$-alkenyl groups, wherein said alkyl groups and alkenyl groups are optionally substituted with at least one OH group;

$R_5$ is chosen from a hydrogen atom, $C_1$–$C_6$-alkyl groups, $C_2$–$C_6$-alkenyl groups and $C_2$–$C_6$-alkynyl groups;

$R_4$, $R_6$, $R_8$ and $R_{10}$, are each independently chosen from hydrogen atoms, $C_1$–$C_6$-alkyl groups, $C_2$–$C_6$-alkenyl groups, $C_2$–$C_6$-alkynyl groups, —$X_2$H groups wherein H is directly bonded to the first atom of $X_2$, and —$X_2R_{12}$ groups wherein $R_{12}$ is directly bonded to the first atom of $X_2$, and optionally $R_4$ and $R_6$ together are a double bonded -$X_2$ group, and optionally $R_8$ and $R_{10}$ together are a double bonded —$X_2$ group, wherein each $X_2$ is independently chosen from oxygen atoms, —NH groups, -N-$C_1$-$C_6$-alkyl groups, —N—$C_2$–$C_6$-alkenyl groups, —N—$C_2$–$C_6$-alkynyl groups and sulfur atoms, wherein each $R_{12}$ is independently chosen from $C_1$–$C_6$-alkyl groups, $C_2$–$C_6$-alkenyl groups, $C_2$–$C_6$-alkynyl groups, aryl groups and acyl groups; and m and n are each independently chosen from 1 and 2; in any of its stereochemical forms and mixtures of these forms in any ratio, and a physiologically acceptable salt or derivative thereof.

2. A compound according to claim 1, wherein $R_7$ is an aminosugar.

3. A compound according to claim 1, wherein $R_7$ has the formula

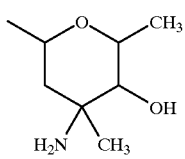

4. A compound according to claim 1, wherein n is 2.

5. A compound according to claim 1, wherein $R_1$ is an aminosugar.

6. A compound according to claim 1, wherein $R_1$ has the formula

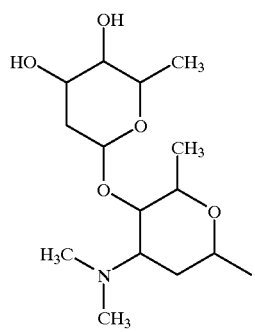

7. A compound according to claim 1, wherein $R_3$ is chosen from groups

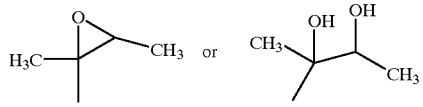

8. A compound according to claim 1, of formula (IA)

IA

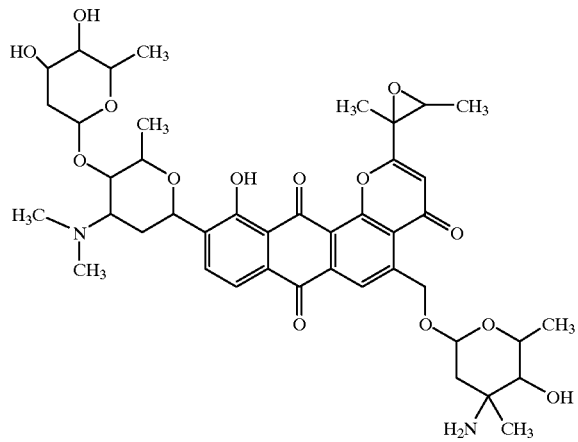

in any of its stereochemical forms and mixtures of these forms in any ratio, and a physiologically acceptable salt or derivative thereof.

9. A compound according to claim 1, of formula (IB)

IB

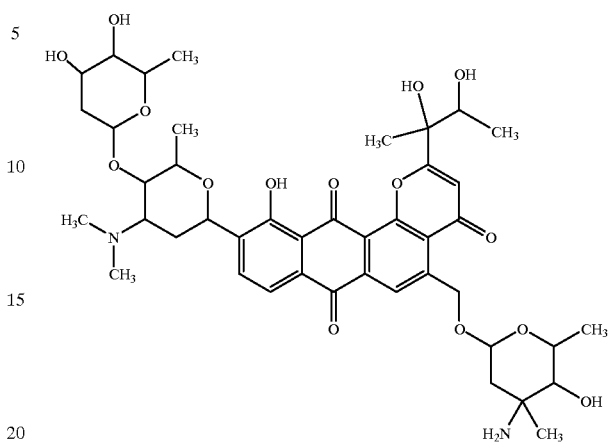

in any of its stereochemical forms and mixtures of these forms in any ratio, and a physiologically acceptable salt or derivative thereof.

10. A compound according to claim 1, of formula (IE)

IE

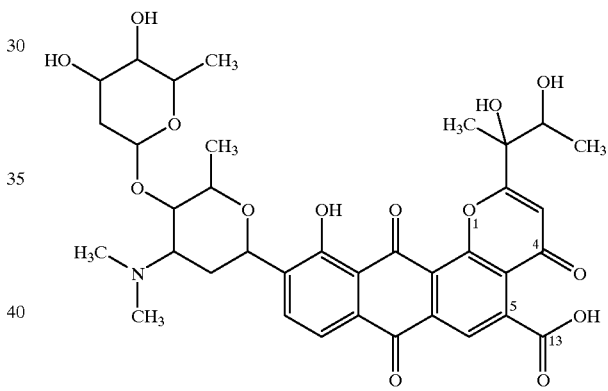

in any of its stereochemical forms and mixtures of these forms in any ratio, and a physiologically acceptable salt or derivative thereof.

11. A compound of formula (I) as claimed in claim 1, obtainable by cultivating Actinomycetales species HAG 003959, DSM 12931, or one of its variants or mutants under suitable conditions in a culture medium until at least one compound of formula (I) is present in the culture medium, followed by isolation of the compound.

12. A compound according to claim 11, wherein said isolated compound is further converted into at least one compound chosen from derivatives and physiological acceptable salts.

13. A composition comprising at least one compound of formula (I) according to claim 1, or a physiologically acceptable salt or derivative, and an acceptable vehicle.

14. A composition according to claim 13, wherein said acceptable vehicle is a pharmaceutically acceptable vehicle.

15. A process for making at least one compound of formula (I) or a physiologically acceptable salt thereof as claimed in claim 1, which comprises cultivating the microorganism Actinomycetales species HAG 003959, DSM 12931, or one of its variants or mutants, under suitable conditions in a culture medium until at least one compound of formula (I) is present in the culture medium, followed by isolation of the compound.

16. A process according to claim 15, wherein said isolated compound is further converted into at least one compound chosen from derivatives and physiological acceptable salts.

17. The process according to claim 15, wherein the cultivation is carried out under aerobic conditions at a temperature between 18 and 35° C. and at a pH between 6 and 8.

18. The process according to claim 15, wherein the compound of formula (I) is converted into a derivative using a reducing agent.

19. A process for inhibiting transcription of at least one double stranded nucleic acid comprising contacting said double stranded nucleic acid with an effective amount of at least one compound of formula (I) as defined in claim 1, or a physiologically acceptable salt or derivative thereof.

20. A process for using at least one compound of formula (I) according to claim 1, or a physiologically acceptable salt or derivative thereof, as a cytostatic comprising contacting a target cell with an effective amount of said compound.

21. A process for treating a colon tumor comprising contacting a colon tumor cell with an effective amount of at least one compound of formula (1) according to claim 1, or a physiologically acceptable salt or derivative thereof.

22. A process for treating a mammary (breast) tumor comprising contacting a mammary tumor cell with an effective amount of at least one compound of formula (I) according to claim 1, or a physiologically acceptable salt or derivative thereof.

23. A process for treating a lung tumor comprising contacting a lung tumor cell with an effective amount of at least one compound of formula (I) according to claim 1, or a physiologically acceptable salt or derivative thereof.

24. A process for treating a prostate tumor comprising contacting a prostate tumor cell with an effective amount of at least one compound of formula (I) according to claim 1, or a physiologically acceptable salt or derivative thereof.

25. A process for treating leukemia comprising contacting a leukemia cell with an effective amount of at least one compound of formula (I) according to claim 1, or a physiologically acceptable salt or derivative thereof.

26. A process for using at least one compound of formula (I) according to claim 1, or a physiologically acceptable salt or derivative thereof, as an antimicrobial comprising contacting a microbe with an effective amount of said compound.

27. Actinomycetales species HAG 003959 (DSM 12931).

* * * * *

UNITED STATES PATENT AND TRADEMARK OFFICE
CERTIFICATE OF CORRECTION

PATENT NO.      : 6,500,936 B2
DATED           : December 31, 2002
INVENTOR(S)     : Laszlo Vertesy et al.

It is certified that error appears in the above-identified patent and that said Letters Patent is hereby corrected as shown below:

<u>Title page,</u>
Item [57], ABSTRACT,
Line 7, "$R_4R_6$," should read -- $R_4$, $R_6$, --.
Line 8, "H;" should read -- H, --.

Signed and Sealed this

Fifteenth Day of April, 2003

JAMES E. ROGAN
*Director of the United States Patent and Trademark Office*